(12) United States Patent
Mizomoto et al.

(10) Patent No.: US 8,136,676 B2
(45) Date of Patent: *Mar. 20, 2012

(54) POLYMERS USEFUL AS MEDICAL MATERIALS

(75) Inventors: Hitoshi Mizomoto, Fuji (JP); Mark Bradley, Edinburgh (GB)

(73) Assignee: University of Southampton, Southampton, Hampshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/660,428

(22) PCT Filed: Aug. 11, 2005

(86) PCT No.: PCT/GB2005/003151
§ 371 (c)(1), (2), (4) Date: Nov. 14, 2007

(87) PCT Pub. No.: WO2006/016163
PCT Pub. Date: Feb. 16, 2006

(65) Prior Publication Data
US 2008/0190843 A1    Aug. 14, 2008

(30) Foreign Application Priority Data
Aug. 13, 2004    (GB) .................................. 0418124.4

(51) Int. Cl.
*B01D 24/00* (2006.01)
*B01D 39/00* (2006.01)
*B01D 71/06* (2006.01)
*B01D 61/00* (2006.01)

(52) U.S. Cl. ............. 210/508; 210/500.22; 210/500.24; 210/500.35; 210/500.36; 210/500.37; 210/500.38; 210/506; 210/507; 210/645

(58) Field of Classification Search ............. 210/500.27, 210/506, 507, 723; 526/72, 317.1, 218.1, 526/219.6; 424/78.08
See application file for complete search history.

(56) References Cited

U.S. PATENT DOCUMENTS

| 4,936,998 A | 6/1990 | Nishimura et al. |
| 7,410,066 B2 * | 8/2008 | Yamada et al. ............... 210/504 |
| 2002/0000403 A1 * | 1/2002 | Tanaka et al. ................. 210/263 |
| 2003/0042209 A1 | 3/2003 | Mori et al. |

FOREIGN PATENT DOCUMENTS

| CA | 2 455 786 | 2/2003 |
| EP | 1 156 067 | 11/2001 |
| EP | 1 192 956 | 4/2002 |
| EP | 1 230 940 | 8/2002 |
| WO | WO03/047655 | * 6/2003 |
| WO | WO 2004/045755 | 6/2004 |

* cited by examiner

*Primary Examiner* — Krishnan S Menon
*Assistant Examiner* — Dirk Bass
(74) *Attorney, Agent, or Firm* — Merchant & Gould P.C.

(57) ABSTRACT

One object of the present invention is to provide polymers suitable for use as medical materials. The present invention provides a polymer useful as a medical material having the general formula $$-(A)_l-(B)_m-(C)_n- \qquad (I)$$

in which A is derived from an alkoxyalkyl (alkyl)acrylate monomer;
B is derived from a monomer containing a primary, secondary, tertiary or quaternary amine group;
C is derived from a non-ionic monomer;
and $l+m+n=100, 0<l, m, n<100$.

17 Claims, No Drawings

POLYMERS USEFUL AS MEDICAL MATERIALS

FIELD OF THE INVENTION

The present invention relates to polymers and their use as biomedical materials in the preparation of separation media for selective separation or purification of specific biological components, for example proteins and cells, from biological fluids. More specifically, the present invention relates to polymers useful as medical materials, such as in the preparation of filtration media for removing leucocytes from whole blood or blood products containing leucocytes, and to filtration media comprising the polymers.

DESCRIPTION OF THE PRIOR ART

The technology of the separation and purification of specific biological components is essential in the biomedical area, because the specific biological components to be separated are existed in the mixture such as blood, bodily fluids, culture and so on. Commonly the separation and purification of biological components involve some forms of chromatography, which has become an essential tool in the laboratory. Some chromatography, which is widely used, is based on the affinity of the biological interaction such as antigen-antibody. The affinity chromatography based on the biological interaction can achieve the high selective separation and purification of biological components. However, there are still major problems, especially the stability and high cost of the biological affinity ligands. On the other hand, the chromatography, which is based on the technology of physicochemical interaction, gives lower selectivity with low cost of physicochemical ligands.

Nowadays several types of polymer membranes are used for the blood purification such as hemodialysis and plasmapheresis. The technique of polymer membrane is based on the size separation. It is hard to separate the target biomolecules, which have similar size of other molecules, by size separation.

Therefore it is desirable to develop the technology for high selective separation and purification of biological components with low cost.

In the field of blood transfusion, which includes inter alia whole blood transfusion, concentrated red cells transfusion, platelet rich plasma transfusion and platelet concentrate transfusion, it is now accepted that depletion of the leucocyte content before transfusion is desirable.

For leucocyte depletion of blood products, filtration processes which remove leucocytes by adhesion of leucocytes onto the fibers of a fibrous filter medium are now widely used. In the filtration process leucocyte removal efficiency is high, the loss of erythrocytes and plasma is low. Also the procedure is simple and can generally be performed at low cost, and at the bedside when necessary.

U.S. Pat. No. 4,330,410 discloses that a filter comprising a mass of fibers having an average diameter of 3 to 10 μm can efficiently entrap leucocytes. EP 0155003 discloses that a non-woven fabric filter comprised of fibers having an average diameter of less than 3 μm not only has a high leucocyte removal efficiency but also can attain an increased rate of treating blood. U.S. Pat. No. 4,936,998 discloses that fibers having surface portions containing non-ionic hydrophilic groups and nitrogen-containing basic functional groups, and having a basic nitrogen content of from 0.2 to 4.0% by weight, have good adhesion to leucocytes while being less adhesive to platelets. Using these fibers as a filtration medium, allows removal of leucocytes to be performed efficiently while keeping loss of platelets to a minimum.

SUMMARY OF THE INVENTION

One object of the present invention is to provide polymers suitable for use as medical materials.

Another object of the present invention is to provide polymers and their use as biomedical materials in the preparation of separation media for selective separation or purification of specific biological components, for example proteins and cells, from biological fluids.

Another object of the present invention is to provide a filter medium useful for selectively removing components from biological fluids, especially for removing leucocytes from blood and blood products.

According to one aspect of the present invention there is provided a polymer having the general formula

$$-(A)_l-(B)_m-(C)_n- \qquad (I)$$

in which A is an alkoxyalkyl(alkyl)acrylate monomer residue;

B is a monomer residue containing a primary, secondary, tertiary or quaternary amine group;

C is a non-ionic monomer residue;

and l+m+n=100, 0<l, m, n<100.

In another aspect the present invention provides a filtration medium in which at least a surface portion is composed of a polymer of the invention.

In a further aspect the present invention provides a filter structure comprising a filter casing and a filtration medium of the invention.

DETAILED DESCRIPTION

Generally the affinity between the material and the biological components such as proteins and cells is affected by surface charge density and hydrophobicity/hydrophilicity balance. Most of cells and proteins are charged because of the functional groups, particularly carboxylic acids, phosphoric acids and amino groups, and the density of charge depends on the type of cells and proteins. Therefore, the affinity with the charge can be utilized for the selective separation and purification of cells and proteins.

On the other hand, the protein and cell contain both hydrophilic and hydrophobic parts.

As a result, they can form the specific interaction such as hydrogen bonding and hydrophobic interaction. The hydrophobicity/hydrophilicity balance of polymeric material can control the protein and cell adsorption.

The polymers of the invention have been found to have an affinity for components of biological fluids, such as blood, so that they can be used for the selective removal, reduction or separation of the components, for example by use as fibers or coatings in filters.

The term "biological fluid" used herein means fluid that contains the specific biological component. For example, the specific biological component is one type of the specific cells, proteins, interferon, cytokines, lymphokine, peptides, genes, nucleic acid, hormones, steroid, enzymes, carbohydrates, cyclodextrin, lipids, antibiotics, or pyrogens. Examples of the biological fluid include blood, plasma, serum, bodily fluid, digestive fluid, urine, or culture fluid.

In particular, the polymers may be used as a component of filters for the selective removal of white blood cells and platelets from blood. Polymers showing high leucodepletion tended to exhibit high human immunoglobulin G (IgG) absorption as well.

The term "filter media" and "filtration media" used herein mean media that can remove, reduce and separate the specific components, and include the membrane, the filter material, the loading material for packed column, and so on.

Typically the monomer residue units are present at 20-80% by mol of A;

10-40% by mol of B;

10-40% by mol of C.

In a useful group of polymers, A is present at about 40 mol %, B is about 30 mol % and C is about 30 mol %.

The main component of the polymer in this invention is based on the monomer A because of the stability in water. The polymer with high contents of monomer B causes the damage of the biological components owing to the high charge density, and the polymer with high content of monomer C has low efficiency for the separation and purification of specific biological components. The polymer with low contents of monomer B and C has low selectivity and efficiency. It has been found that the polymers with 20-80 mol % of A, 10-40 mol % of B and 10-40 mol % of C achieve the high selectivity and efficiency for the separation and purification of specific biological components.

The monomer residue A may be derived from an alkoxyalkyl(alkyl)acrylate monomer.

As the monomer residue A, units of structure D are especially suitable:

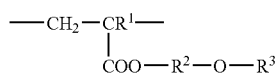

D in which $R^1$ is H or a lower alkyl group;

$R^2$ is $CH_2$—$CH_2$, $CH_2$—$CHR^a$, $CHR^a$—$CH_2$, $CHR^a$—$CHR^b$, $CHR^a$—$CR^bR^c$, $CR^aR^b$—$CHR^c$, $CR^aR^b$—$CR^cR^d$, $(CH_2)_e$, where e=2-6, and $R^a$, $R^b$, $R^c$, $R^d$ are lower alkyl groups and $R^a$, $R^b$, $R^c$ and $R^d$ maybe the same or different;

$R^3$ is a lower alkyl, phenyl or substituted phenyl group.

Typical examples of suitable monomers from which A may be derived include alkoxy(meth)acrylates.

Suitable alkoxy(meth)acrylates include 2-methoxyethyl methacrylate, 2-methoxyethyl acrylate, 2-ethoxyethyl methacrylate, 2-ethoxyethyl acrylate, 2-phenoxyethyl methacrylate, 2-phenoxyethyl acrylate, 2-(2-methoxyethoxy)ethyl methacrylate, 2-(2-methoxyethoxy)ethyl acrylate, 2-(2-ethoxyethoxy)ethyl methacrylate, and 2-(2-ethoxyethoxy)ethyl acrylate.

Unless indicated otherwise, references herein to "alkyl" groups means lower alkyl groups i.e. having 1-6 carbon atoms, which may be branched or linear. The group "substituted phenyl" is typically phenyl substituted by one or more lower alkyl groups.

The monomer residue B may be derived from an amine-containing ethylenically unsaturated monomer, preferably a vinyl compound, and most preferably an acrylate derivative.

As the monomer residue B, units of structure E are especially suitable:

E in which $R^4$, $R^6$, $R^7$ are independently H, lower alkyl, phenyl or substituted phenyl groups;

$R^5$ is $CH_2$—$CH_2$, $CHR$—$CH_2$, $CH_2$—$CHR^a$, $CHR^a$—$CH_2$, $CHR^a$—$CHR^b$, $CHR^a$—$CR^bR^c$, $CR^aR^b$—$CHR^c$, $CR^aR^b$—$CR^cR^d$, $(CH_2)_e$, where e=2-6, and $R^a$, $R^b$, $R^c$, $R^d$ are lower alkyl groups and $R^a$, $R^b$, $R^c$ and $R^d$ maybe the same or different;

X is O or $NR^f$, where $R^f$ is H or a lower alkyl group.

Typical examples of suitable monomers from which B may be derived include aminoalkyl(alkyl)acrylates and aminoalkyl(alkyl)acrylamides.

Suitable aminoalkyl(alkyl)acrylates include dialkylaminoalkyl(meth)acrylates, especially 2-(diethylamino)ethyl methacrylate, 2-(diethylamino)ethyl acrylate, 2-(dimethylamino)ethyl methacrylate, 2-(dimethylamino)ethyl acrylate, 3-(diethylamino)propyl methacrylate, 3-(diethylamino)propyl acrylate, 3-(dimethylamino)propyl methacrylate and 3-(dimethylamino)propyl acrylate.

Suitable aminoalkyl(alkyl)acrylamides include dialkylaminoalkyl(meth)acrylamides, especially N-[3-(dimethylamino)ethyl]methacrylamide, N-[3-(dimethylamino)ethyl]acrylamide, N-[3-(diethylamino)ethyl]methacrylamide, N-[3-(diethylamino)ethyl]acrylamide, N-[3-(dimethylamino)propyl]methacrylamide, N-[3-(dimethylamino)propyl]acrylamide, N-[3-(diethylamino)propyl]methacrylamide and N-[3-(diethylamino)propyl]acrylamide.

The monomer residue C may be derived from an ethylenically unsaturated monomer, preferably a vinyl compound, and most preferably an acrylate derivative, although other vinyl monomers such as styrene may also be used.

As the monomer residue C, units of structure F are especially suitable:

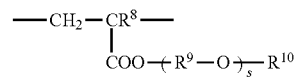

F1

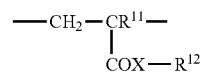

F2

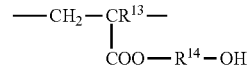

F3

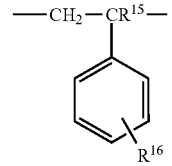

F4 in which $R^8$, $R^{11}$, $R^{13}$, $R^{15}$, $R^{16}$ are independently selected from H, lower alkyl, phenyl or substituted phenyl groups;

$R^9$, $R^{14}$ are independently selected from $CH_2$—$CH_2$, $CH_2$—$CHR^a$, $CHR^a$—$CH_2$, $CHR^a$—$CHR^b$, $CHR^a$—$CR^bR^c$, $CR^aR^b$—$CHR^c$, $CR^aR^b$—$CR^cR^d$, $(CH_2)_e$, where e=2-6, and $R^a$, $R^b$, $R^c$, $R^d$ are lower alkyl groups and $R^a$, $R^b$, $R^c$ and $R^d$ maybe the same or different;

$R^{10}$ is a lower alkyl, phenyl or substituted phenyl group.

$R^{12}$ is H, a lower alkyl, phenyl, substituted phenyl or 1,1-dimethyl-3-oxobutyl group;

s is 0 or s≧2;

X is O or $NR^f$, where $R^f$ is H or a lower alkyl group.

Typical examples of suitable monomers from which C may be derived include alkyl(alkyl)acrylates, especially alkyl (meth)acrylates; hydroxyalkyl(alkyl)acrylates, especially hydroxyalkyl(meth)acrylates; alkyl(alkyl)acrylamides, especially alkyl(meth)acrylamides; poly(alkylene glycol)alkyl ether(alkyl)acrylates, especially poly(ethylene glycol)alkyl ether(meth)acrylates; and styrenes.

Suitable alkyl(meth)acrylates include methyl methacrylate, methyl acrylate, ethyl methacrylate, ethyl acrylate, isopropyl methacrylate, isopropyl acrylate, n-propyl methacrylate, n-propyl acrylate, isobutyl methacrylate, isobutyl acrylate, t-butyl methacrylate, t-butyl acrylate, hexyl methacrylate, hexyl acrylate, cyclohexyl methacrylate, cyclohexyl acrylate, 2-ethylhexyl acrylate, 2-ethylhexyl methacrylate.

Suitable hydroxyalkyl(meth)acrylates include 2-hydroxyethyl methacrylate, 2-hydroxyethyl acrylate, hydroxypropyl methacrylate, hydroxypropyl acrylate, hydroxybutyl methacrylate and hydroxybutyl acrylate.

Suitable alkyl(meth)acrylamides include dimethyl acrylamide and dimethyl methacrylamide Suitable poly(ethylene glycol)alkyl ether(meth)acrylates include di(ethylene glycol)ethyl ether methacrylate.

Acrylate and acrylamide units containing dimethyl oxobutyl groups may also be used, such as 1,1-dimethyl-3-oxobutyl acrylamide (diacetone acrylamide).

A favoured group of polymers in accordance with the invention are polymers having the structure $$—(D)_o—(E)_p—(F)_q— \quad (II)$$

in which

D is $—CH_2—CR^1—$ with $COO—R^2—O—R^3$

E is $—CH_2—CR^4—$ with $COX—R^5—N(R^6)—R^7$

F is selected from

F1: $—CH_2—CR^8—$ with $COO—(R^9—O)_s—R^{10}$

F2: $—CH_2—CR^{11}—$ with $COX—R^{12}$

F3: $—CH_2—CR^{13}—$ with $COO—R^{14}—OH$

F4: $—CH_2—CR^{15}—$ with phenyl bearing $R^{16}$ in which $R^1$ is H or a lower alkyl group;

$R^3$, $R^{10}$ are independently lower alkyl, phenyl or substituted phenyl groups;

$R^4$, $R^6$, $R^7$, $R^8$, $R^{11}$, $R^{13}$, $R^{15}$, $R^{16}$ are independently H, lower alkyl, phenyl or substituted phenyl groups;

$R^2$, $R^5$, $R^9$, $R^{14}$ are independently selected from $CH_2—CH_2$, $CH_2—CHR^a$, $CHR^a—CH_2$, $CHR^a—CHR^b$, $CHR^a—CR^bR^c$, $CR^aR^b—CHR^c$, $CR^aR^b—CR^cR^d$, $(CH_2)_e$, where e=2-6, and $R^a$, $R^b$, $R^c$, $R^d$ are lower alkyl groups and $R^a$, $R^b$, $R^c$ and $R^d$ may be the same or different;

$R^{12}$ is H, a lower alkyl, phenyl, substituted phenyl or 1,1-dimethyl-3-oxobutyl group;

s is 0 or s≧2;

X is O or $NR^f$, where $R^f$ is H or a lower alkyl group;

and o+p+q=100, 0<o, p, q<100.

The preferred group of polymers of the invention is derived from

A: an alkoxyalkyl(meth)acrylate;

B: one or more of a N,N-dialkylaminoalkyl(meth)acrylate and a N,N-dialkylaminoalkyl(meth)acrylamide C: one or more of an alkyl(meth)acrylate, a poly(ethylene glycol) alkyl ether(meth)acrylate, a methacrylamide hydroxyalkyl(meth)acrylate, and styrene.

The preferred polymer is derived from:

A: methoxyethyl(meth)acrylate

B: one or more of N,N-diethylaminoethyl(meth)acrylate, N,N-dimethylaminoethyl(meth)acrylate and N,N-dimethylaminopropyl(meth)acrylamide C: one or more of methyl methacrylate, di(ethylene glycol) ethyl ether(meth)acrylate, N-(1,1-dimethyl-3-oxobutyl)-(meth)acrylamide, dimethyl(meth)acrylamide, 2-hydroxyethyl(meth)acrylate, and styrene.

In recent years, the concept of combinatorial chemistry has spread into a wide range of fields, such as material science;, biotechnology and catalyst design. The combinatorial strategies are appreciate for the complex system concerning with multiple factors. Combinatorial and high throughput methodologies, in which an extremely increased number of experiments are performed, will lead to new discoveries.

Nowadays several combinatorial approaches have been applied to the development of functional polymers. The technique of parallel synthesis and high throughput screening for physical and chemical properties of polymer are useful to accelerate the research. Polymerisations in this invention were carried out with up to twelve parallel reactions at the same time, in a RADLEYS CAROUSEL REACTION STATION (Radleys Discovery Technologies Ltd.) which can work with water-cooling and under nitrogen. In order to determine the molecular weight of the polymer, high throughput gel permeation chromatography (HT-GPC) was performed with a HP1090 Liquid Chromatograph equipped with a refractive index detector (Hewlett Packard Co., Ltd.). PMMA (Polymer Laboratories Co., Ltd.) were used as standards, and the column used was a PLgel 5 μm MIXED-C 300×7.5 mn (Polymer Laboratories Co., Ltd.). NMP or DMF were used as the mobile phase at a flow rate of 1.0 mL/min, and a polymer sample could be measured in about 12 min (5 samples/hr) using HT-GPC.

The polymers of this invention may be synthesised by a free radical polymerisation. Typically a mixture of initiator, for example azo-bis-isobutyronitrile, monomers and solvent, for example dimethylformamide, are mixed under nitrogen, and polymerisation is carried out at elevated temperature, for example 60-80° C. After the reaction, the product may be precipitated by addition into a poor solvent (for example a mixture of cyclohexane, hexane and/or diethyl ether) to obtain a solid. The resultant polymer may then be washed with hexane, cyclohexane and/or diethyl ether, or reprecipitated, and dried under vacuum.

For further processing of the polymer as described below, the polymer is suitably prepared so as to have a number average molecular weight of from 5,000-5,000,000.

The charge density of the polymer in this invention can be controlled by the type and amount of cationic monomer B, and also the hydrophilicity/hydrophobicity can be controlled by the type and amount of monomer C.

Generally the biological components are adsorbed on the specifically charged and hydrophobic surface. In the case of leucocyte, the leucocyte, which is negatively charged, is adsorbed on the cationic and moderate hydrophobic surface. Lower selectivity and less adsorption of leucocyte onto the non-charged hydrophilic polymer are observed, and highly charged and hydrophobic polymer gives the damage of the leucocyte and other cells such as erythrocyte to form the cell activation and destruction.

In another aspect the present invention provides a filter medium in which at least the surface portion comprises a polymer of this invention. The filter medium may be composed of the polymer but more conveniently the surface of a support medium is coated with the polymer. The support may be for example in the form of a membrane or fibers. The employment of fibers in the filter medium of the present invention is preferred because a fiber has a large area per unit weight, which is ideal for efficiently removing leucocytes, and that fibers can easily be fabricated into a filter form.

As long as the peripheral surface portion of the fiber or membrane is made of a polymer of the invention, the fiber or membrane structure may be either such that the body portion of the fiber or membrane is comprised of a substance which is different in chemical composition from that of the peripheral surface portion, or such that the entire fiber or membrane is comprised of the copolymer. From the viewpoints of ease in manufacturing and cost in production, the former is preferable. It is preferred that a base fiber or membrane is first prepared using a general purpose polymer material conventionally used for producing fibers or membranes, and then a surface portion of the copolymer formed thereon. This is more advantageous than a method in which the entire fiber or membrane is prepared from the polymer.

Typically the peripheral surface portion is formed by coating the copolymer on the base fiber material constituting the body portion. However other methods of forming a surface layer of copolymer, such as forming the copolymer on the base fiber by surface graft polymerization, may also be used.

Examples of suitable base fibers include synthetic fibers such as polyester fibers, polyamide fibers, polyacrylonitrile fibers, polymethylmethacrylate fibers, polyethylene fibers and polypropylene fibers, semi-synthetic fibers such as cellulose acetate fibers, regenerated fibers such as cuprammonium rayon fibers, viscose rayon fibers, and viscose staple fibers, natural fibers such as cotton fibers, silk and wool, inorganic fibers such as glass fibers and carbon fibers.

The surface portion of copolymer may suitably have an average thickness of about 10 angstroms or more. If the thickness is less than 10 angstroms, it becomes difficult for the body portion to be completely covered by the copolymer. There is particularly no upper limit for the average thickness. However, if the average thickness is 1 µm or more, the cost for the formation of the peripheral surface portion made of polymer becomes high and loss of copolymer from the surface portion is possible when the mechanical strength of the formed peripheral surface portion is low. Therefore a typical range of the average thickness of the surface portion layer is from 40 angstroms to 400 angstroms.

In producing the filter medium of the present invention by a method in which the above-mentioned type of polymer material is coated on fibers constituting the body portion, the fiber may be dipped in a solution prepared by dissolving the polymer material in a suitable solvent, and then surplus solution is removed by, e.g., mechanical compression, gravity or centrifugation, followed by drying in dry gas or under vacuum at room temperature or at elevated temperatures.

Before coating, the surface of the base fiber may be treated with appropriate chemicals, in order to facilitate the adhesion between the polymer material and the fiber. Further, after the coating, the polymer-coated fiber may be subjected to heat treatment, in order to enhance the adhesion between the fiber and the above-mentioned polymer material or to cause a crosslinking reaction in the coated polymer material for stabilizing the surface portion. In addition, the coating may be conducted simultaneously with, or after the spinning of the fiber. Further, in the case where the filter medium of the present invention is to be used as a filter for removing leucocytes in the form of a woven or non-woven fabric, the coating of the above-mentioned polymer material may be conducted before or after the fabrication of the fibers into the woven or non-woven fabric form.

With respect to the fibers of the filter medium of the present invention, the average fiber diameter is preferably 10 µm or less, more preferably less than 3 µm, since the smaller the average fiber diameter, the larger the leucocyte removing ability per unit weight of the fiber. However, if the average fiber diameter is less than 0.3 µm, the filter made up of the fibers is not only likely to be clogged, and but also likely to damage the cell wall of erythrocytes, causing hemolysis. Therefore, the average fiber diameter is preferably 0.3 µm or more. In this connection, from the viewpoints of the leucocyte removing ability etc., fibers having an average diameter of from 0.5 to 2.0 µm are most preferred.

In using a fibrous filter medium of the present invention as a leucocyte removing filter, it may be used in the form of a simple mass of fibers or in the form of a woven or non-woven fabric. However, the woven or non-woven fabric form is preferable because with this form, in general, the leucocyte removing performance per unit weight of the filter is high and, in addition, the filter thickness in the direction of the filtration flow can be reduced, so that the pressure loss may be reduced, enabling the blood processing rate to be increased with advantages. Further, in the viewpoint of ease in manufacturing (particularly when the fiber diameter is small), the non-woven fabric form is most preferably employed.

When the filter medium of the present invention is employed as a filter for removing leucocytes, the filter medium of the present invention may be packed in a known appropriate filter container for blood filtration which has an inlet and an outlet. The bulk density of the packed filter medium may be varied according to the fiber diameter, but is preferably 0.02 to 0.7 g/cm$^3$. The "bulk density" used herein means a value obtained by dividing the weight of the effective portion of the filter medium packed in a container by the volume of space occupied by the effective portion. When the filter medium of the present invention is used in the form of a woven or non-woven fabric, it may be used as a single sheet of fabric or as a laminate of a plurality of sheets of fabrics depending on the thickness of the sheet. When a laminate of a plurality of sheets is used, the number of sheets is not strictly limited but is usually several to several tens depending on the blood filtration conditions.

Further sheets of non-woven fabric may be added to the stack as pre- and post-filters. To remove cell debris and platelet aggregates. A preferred construction of filter is disclosed in European Patent 0155003 (Asahi Medical—SEPACELL filter), the entire disclosure of which is incorporated herein by reference.

The filtration medium which has at least a surface portion composed of a polymer of the invention can be utilized in the biomedical, medicinal, pharmaceutical, agricultural, cosmetic, food industrial, and chemical field.

The invention is further illustrated by the following Examples:

EXAMPLE 1

Terpolymer, (MEMA, DEGMEMA, DEAEA (40/30/30)

2-Methoxyethylmethacrylate (MEMA, 0.50 mL, 3.4 mmol), di(ethylene glycol)ethyl ether methacrylate (DEG- MEMA, 0.48 mL, 2.6 mmol), and 2-(diethylamino)ethyl acrylate (DEAEA, 0.48 mL, 2.6 mmol), azo-bis-isobutyronitrile, (AIBN, 3.5 mg, 0.022 mmol) as initiator, and toluene (4.4 mL) as solvent were mixed under nitrogen. In this case, the total monomer concentration was 25 vol. %, and the initiator amount was calculated as $\frac{1}{400}$ of the total monomer. Polymerisation was carried out at 60° C. under nitrogen overnight. After the reaction, the product was precipitated by dropwise addition into a mixture of hexane and diethyl ether. The polymer was dissolved in tetrahydrofuran (THF) and reprecipitated with hexane and diethyl ether. The product was dried under vacuum at 40° C. overnight. White solid, 0.95 g (67% yield), Mw: 92,600 Mn: 30,700 MWD 3.0

EXAMPLE 2

Terpolymer, (MEMA, DMAA, DEAEMA (40/30/30)

2-Methoxyethylmethacrylate (MEMA, 0.50 mL, 3.4 mmol), dimethylacrylamide (DMAA, 0.27 mL, 2.6 mmol), and 2-(diethylamino)ethyl methacrylate (DEAEMA, 0.52 mL, 2;6 mmol), azo-bis-isobutyronitrile, (AIBN, 3.5 mg, 0.022 mmol) as initiator, and dimethylformamide (DMF, 3.85 mL) as solvent were mixed under nitrogen. In this case, the total monomer concentration was 25 vol. %, and the initiator amount was calculated as $\frac{1}{400}$ of the total monomer. Polymerisation was carried out at 60° C. under nitrogen overnight. After the reaction, the product was precipitated by dropwise addition into a mixture of hexane and diethyl ether. The polymer was dissolved in tetrahydrofuran (THF) and reprecipitated with hexane and diethyl ether. The product was dried under vacuum at 40° C. overnight. White solid, 1.1 g (85% yield), Mw: 95,300, Mn: 28,500 MWD 3.3

EXAMPLE 3

Terpolymer, (MEMA, DAAA, DEAEA (40/30/30)

2-Methoxyethylmethacrylate (MEMA, 0.70 mL, 4.8 mmol), diacetone acrylamide (DAAA, 0.612 g, 3.6 mmol), and 2-(diethylamino)ethyl acrylate (DEAEA, 0.672 mL, 3.6 mmol), azo-bis-isobutyronitrile, (AIBN, 4.9 mg, 0.030 mmol) as initiator, and dimethylformamide (DMF, 2.0 mL) as solvent were mixed under nitrogen. In this case, the total monomer concentration was 50 vol. %, and the initiator amount was calculated as $\frac{1}{400}$ of the total monomer. Polymerisation was carried out at 60° C. under nitrogen overnight. After the reaction, the product was precipitated by dropwise addition into a mixture of hexane and diethyl ether. The polymer was dissolved in tetrahydrofuran (THF) and reprecipitated with hexane and diethyl ether. The product was dried under vacuum at 40° C. overnight. White solid, 1.7 g (88% yield), Mw: 101,000, Mn: 29,400 MWD 3.4

EXAMPLES 4-89

Using analogous procedures to those described above for Examples 1-3, further copolymers were prepared using the monomers and proportions set out in Table 1 below. The monomers used (in addition to those already identified in Examples 1-3) are as follows:
MMA: methyl methacrylate
HEMA: 2-hydroxyethyl methacrylate
HEA: 2-hydroxyethyl acrylate
St: styrene

TABLE 1

| | Polymer structure | | | Ratio (mol) | | | Polymer property Molecular weight | | |
|---|---|---|---|---|---|---|---|---|---|
| Example No | Monomer (1) | Monomer (2) | Monomer (3) | M (1) | M (2) | M (3) | Mw | Mn | MWD |
| 1 | MEMA | DEAEA | DEGMEMA | 40 | 30 | 30 | 92600 | 30700 | 3.02 |
| 2 | MEMA | DEAEMA | DMAA | 40 | 30 | 30 | 95300 | 28500 | 3.34 |
| 3 | MEMA | DEAEA | DAAA | 40 | 30 | 30 | 101000 | 29400 | 3.44 |
| 4 | MEMA | DEAEMA | DEGMEMA | 40 | 30 | 30 | 165000 | 41200 | 4.00 |
| 5 | MEMA | DEAEMA | DEGMEMA | 60 | 10 | 30 | 231000 | 46700 | 4.95 |
| 6 | MEMA | DEAEMA | DEGMEMA | 60 | 30 | 10 | 111000 | 36100 | 3.07 |
| 7 | MEMA | DEAEMA | DEGMEMA | 80 | 10 | 10 | 141000 | 42200 | 3.34 |
| 8 | MEMA | DEAEA | DEGMEMA | 60 | 10 | 30 | 206000 | 47300 | 4.36 |
| 9 | MEMA | DEAEA | DEGMEMA | 60 | 30 | 10 | 145000 | 31000 | 4.68 |
| 10 | MEMA | DEAEA | DEGMEMA | 80 | 10 | 10 | 152000 | 40600 | 3.74 |
| 11 | MEMA | DEAEMA | HEA | 40 | 30 | 30 | 74700 | 23000 | 3.25 |
| 12 | MEMA | DEAEMA | HEA | 60 | 10 | 30 | 149000 | 31400 | 4.75 |
| 13 | MEMA | DEAEMA | HEA | 60 | 30 | 10 | 105000 | 30100 | 3.49 |
| 14 | MEMA | DEAEMA | HEA | 80 | 10 | 10 | 187000 | 41100 | 4.55 |
| 15 | MEMA | DEAEA | HEA | 40 | 30 | 30 | 73800 | 21300 | 3.46 |
| 16 | MEMA | DEAEA | HEA | 60 | 10 | 30 | 139000 | 29100 | 4.78 |
| 17 | MEMA | DEAEA | HEA | 60 | 30 | 10 | 77200 | 18800 | 4.11 |
| 18 | MEMA | DEAEA | HEA | 80 | 10 | 10 | 145000 | 32600 | 4.45 |
| 19 | MEMA | DEAEMA | HEMA | 40 | 30 | 30 | 200000 | 42900 | 4.66 |
| 20 | MEMA | DEAEMA | HEMA | 60 | 10 | 30 | 362000 | 57300 | 6.32 |
| 21 | MEMA | DEAEMA | HEMA | 60 | 30 | 10 | 146000 | 37100 | 3.94 |
| 22 | MEMA | DEAEMA | HEMA | 80 | 10 | 10 | 201000 | 46400 | 4.33 |
| 23 | MEMA | DEAEA | HEMA | 40 | 30 | 30 | 83400 | 22300 | 3.74 |
| 24 | MEMA | DEAEA | HEMA | 60 | 10 | 30 | 270000 | 48500 | 5.57 |
| 25 | MEMA | DEAEA | HEMA | 60 | 30 | 10 | 94500 | 30900 | 3.06 |
| 26 | MEMA | DEAEA | HEMA | 80 | 10 | 10 | 178000 | 37800 | 4.71 |
| 27 | MEMA | DEAEMA | DMAA | 60 | 10 | 30 | 117000 | 34800 | 3.36 |
| 28 | MEMA | DEAEMA | DMAA | 60 | 30 | 10 | 101000 | 32800 | 3.08 |
| 29 | MEMA | DEAEMA | DMAA | 80 | 10 | 10 | 133000 | 40400 | 3.29 |
| 30 | MEMA | DEAEA | DMAA | 40 | 30 | 30 | 73800 | 26100 | 2.83 |
| 31 | MEMA | DEAEA | DMAA | 60 | 10 | 30 | 106000 | 32100 | 3.30 |
| 32 | MEMA | DEAEA | DMAA | 60 | 30 | 10 | 78800 | 26400 | 2.98 |
| 33 | MEMA | DEAEA | DMAA | 80 | 10 | 10 | 114000 | 35400 | 3.22 |
| 34 | MEMA | DEAEMA | DAAA | 40 | 30 | 30 | 130000 | 33400 | 3.89 |

TABLE 1-continued

| | Polymer structure | | | Ratio (mol) | | | Polymer property | | |
|---|---|---|---|---|---|---|---|---|---|
| | | | | | | | Molecular weight | | |
| Example No | Monomer (1) | Monomer (2) | Monomer (3) | M (1) | M (2) | M (3) | Mw | Mn | MWD |
| 35 | MEMA | DEAEMA | DAAA | 60 | 10 | 30 | 194000 | 44400 | 4.37 |
| 36 | MEMA | DEAEMA | DAAA | 60 | 30 | 10 | 169000 | 38700 | 4.37 |
| 37 | MEMA | DEAEMA | DAAA | 80 | 10 | 10 | 243000 | 46600 | 5.21 |
| 38 | MEMA | DEAEA | DAAA | 60 | 10 | 30 | 183000 | 36300 | 5.04 |
| 39 | MEMA | DEAEA | DAAA | 60 | 30 | 10 | 70200 | 24100 | 2.91 |
| 40 | MEMA | DEAEA | DAAA | 80 | 10 | 10 | 211000 | 43400 | 4.86 |
| 41 | MEMA | DEAEMA | MMA | 40 | 30 | 30 | 167000 | 46500 | 3.59 |
| 42 | MEMA | DEAEMA | MMA | 60 | 10 | 30 | 205000 | 54100 | 3.79 |
| 43 | MEMA | DEAEMA | MMA | 60 | 30 | 10 | 219000 | 51700 | 4.24 |
| 44 | MEMA | DEAEMA | MMA | 80 | 10 | 10 | 244000 | 58300 | 4.19 |
| 45 | MEMA | DEAEA | MMA | 40 | 30 | 30 | 99200 | 31400 | 3.16 |
| 46 | MEMA | DEAEA | MMA | 60 | 10 | 30 | 179000 | 51147 | 3.50 |
| 47 | MEMA | DEAEA | MMA | 60 | 30 | 10 | 106000 | 33300 | 3.18 |
| 48 | MEMA | DEAEA | MMA | 80 | 10 | 10 | 208000 | 49100 | 4.24 |
| 49 | MEMA | DEAEMA | St | 40 | 30 | 30 | 72100 | 35700 | 2.02 |

Protein Adsorption

The adsorption interaction between the polymer of this invention and protein was determined in accordance with the following microarray analysis.

On the surface of a glass plate of $75 \times 10^{-3}$ m in length and $25 \times 10^{-3}$ m in width, a gold deposition film of 3000 nm in thickness was previously formed by a vacuum evaporation device, CFS-8E-55 (SHIBAURA MECHATRONICS Co. Ltd.). Sample polymers and reference samples, namely, vinylidene chloride/acrylonitrile copolymer and cellulose acetate that were selected from a polymer sample kit #205 (Scientific Polymer Products Inc.) were dissolved in N-methyl-2-pyrrolidon in a concentration of 10 g/dm$^3$ to obtain individual polymer solutions. The polymer solutions were added to a 384-well polypropylene plate (Genetix Ltd.).

On the glass plate having a gold deposition film coated on the surface, the sample polymer solutions and the reference polymer solutions were dropped by means of an arrayer device, Q Array mini (Genetix Ltd.). More specifically, a sample polymer solution was spotted 5 times on the same position by using a standard solid (no hollow) pin of 150 μm (Genetix Ltd.). To remove the remaining solvent, each glass plates was placed in a vacuum dryer and dried at 50° C. for 16 hours.

A GENEFRAME (ABgene Ltd.) was placed around the printed glass plate (used to give a uniform layer thickness across the array), and $3.0 \times 10^{-7}$ m$^3$ of the protein solution was added within the frame. The slide was then sealed with the supplied polyester cover-slip (ABgene Ltd.) and the whole assembly was incubated for 5 mins at room temperature. After the incubation the polyester sheet and the frame was removed, and the glass plate was washed with deionized water, 0.01 M phosphate buffer solution (pH 7.4) and deionized water in this order, followed by being dried with nitrogen gas at room temperature.

The Alexa Fluor 647 (Molecular Probes, Inc.)-conjugated human fibrinogen (Sigma-Aldrich Co. Ltd.) solutions (25 μg/mL) and Alexa Fluor 546 (Molecular Probes, Inc.)-conjugated glycophorin A (Sigma-Aldrich Co. Ltd.) solution (12.5 μg/mL) were prepared in 1% whole human serum/phosphate buffered saline (pH7.4), and they were used as the protein solution for the microarray analysis.

The fluorescent intensity of the protein adsorbed onto a polymer spot on the glass plate was measured by a fluorescence analysis device, Bioanalyzer 4f/4s scanner (LaVision BioTech). The measurement data of fluorescent intensity was analyzed by the analysis/calculation software, FIPS software (LaVision BioTech).

The fluorescence intensities, which represent protein adsorption amounts of vinylidene chloride/acrylonitrile copolymer and cellulose acetate as reference samples are shown in Table 2 below.

TABLE 2

| Polymer type | Fibrinogen | Glycophorin A |
|---|---|---|
| Cellulose acetate | 81900 | 50300 |
| Vinylidene chloride/acrylonitrile copolymer | 738000 | 777000 |

The corresponding properties for certain polymers of this invention that were tested are reported in Table 3 below.

TABLE 3

| | Polymer structure | | | Ratio (mol) | | | Protein adsorption | |
|---|---|---|---|---|---|---|---|---|
| Example No | Monomer (1) | Monomer (2) | Monomer (3) | M (1) | M (2) | M (3) | Fibrinogen | Glycophorin A |
| 45 | MEMA | DEAEA | MMA | 40 | 30 | 30 | 923,000 | 3,308,000 |
| 46 | MEMA | DEAEA | MMA | 60 | 10 | 30 | 197,000 | 858,000 |
| 48 | MEMA | DEAEA | MMA | 80 | 10 | 10 | 60,900 | 479,000 |

Preparation of Blood Filters

A filter base material was prepared by coating selected polymers from Example 1-102 onto a non-woven fabric (thickness: 0.20 mm, polyethylene terephthalate fiber with an average fiber diameter of 1.2 micrometers). The polymer coated non-woven fabric was clipped into circles with a diameter of 20 mm, and a filter holder was loaded with a stack of 9 sheets.

Blood Assay

Human fresh whole blood was passed though the filter stack at a fixed rate-of-flow 0.74 mL/min using a syringe pump, and the filtrate (4 mL) was collected. Leucocyte concentration was measured by a LEUCOCOUNT kit, a flow cytometer—FACSCALIBUR, and analysis software—CELL QUEST (BD Bioscience, USA). Platelet concentration was measured by an automatic blood cell counters, MAX A/L-RETIC (Beckman Coulter, USA).

Leukodepletion ability and platelet recovery were calculated from the formulae below:

Leukodepletion ability(−Log)=−Log(leukocyte concentration after the filtration/leukocyte concentration before the filtration)

Platelet(PLT) recovery(%)=(platelet concentration after filtration/platelet concentration after filtration)×100

The tendency to produce haemolysis was evaluated by removing blood cell components from the filtered blood by centrifugation (1500 rpm, 10 min), and then detecting haemoglobin by measuring absorbance at 576 nm.

As a positive control, a polymer currently used for blood filters (HM3—Asahi Chemical Corporation) was used. The difference of leukodepletion ability from the positive control was calculated to reduce the error between each experiment.

For reference, the properties for HM3 are:

|  | Ave. | (Standard deviation) |
|---|---|---|
| Leuco-depletion ability (−log) | 2.98 | (0.38) |
| Platelet recovery (%) | 1.6 | (2.7) |
| Hemolysis (ABS at 576 nm) | 0.25 | (0.20) |

The corresponding properties for certain polymers of this invention which were tested are reported in Table 4 below.

TABLE 4

| Example No. | Polymer structure | | | | | | Blood test | | |
|---|---|---|---|---|---|---|---|---|---|
| | Monomer (1) | Monomer (2) | Monomer (3) | M (1) | M (2) | M (3) | Leuko-depletion (−HM3) average | Platelet recovery average | Haemolysis average |
| 1 | MEMA | DEAEA | DEGMEMA | 40 | 30 | 30 | 0.61 | 0.31 | 0.65 |
| 2 | MEMA | DEAEMA | DMAA | 40 | 30 | 30 | 0.45 | 0.85 | 0.10 |
| 4 | MEMA | DEAEMA | DEGMEMA | 40 | 30 | 30 | 0.65 | 0.47 | 0.48 |
| 11 | MEMA | DEAEMA | HEA | 40 | 30 | 30 | 0.52 | 0.63 | 0.26 |
| 19 | MEMA | DEAEMA | HEMA | 40 | 30 | 30 | 0.27 | 1.69 | 0.22 |
| 28 | MEMA | DEAEMA | DMAA | 60 | 30 | 10 | 0.73 | 0.20 | 0.97 |
| 32 | MEMA | DEAEA | DMAA | 60 | 30 | 10 | 0.24 | 0.00 | 0.08 |
| 34 | MEMA | DEAEMA | DAAA | 40 | 30 | 30 | 0.73 | 0.55 | 0.91 |
| 41 | MEMA | DEAEMA | MMA | 40 | 30 | 30 | 0.57 | 0.20 | 0.32 |
| 47 | MEMA | DEAEA | MMA | 60 | 30 | 10 | 0.66 | 0.24 | 0.95 |
| 49 | MEMA | DEAEMA | St | 40 | 30 | 30 | 0.23 | 8.47 | 0.18 |

The invention claimed is:

1. A separation system configured to remove a leukocyte from a liquid medium; the system comprising:

a container defining an inlet, an outlet, and a volume of space; a separation medium occupying at least a portion of the volume of space; the container being configured for contacting the separation medium with the liquid medium;

the separation medium comprising a surface portion; the surface portion comprising a ternary polymer of the general formula:

in which

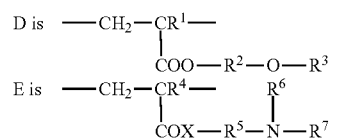

F is selected from

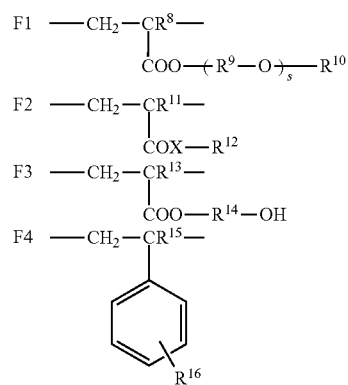

in which $R^1$ is H or a lower alkyl group;

$R^3$, $R^{10}$ are independently lower alkyl, phenyl or substituted phenyl groups;

$R^4$, $R^6$, $R^7$, $R^8$, $R^{11}$, $R^{13}$, $R^{15}$, $R^{16}$ are independently H, lower alkyl, phenyl or substituted phenyl groups;

$R^2$, $R^5$, $R^9$, $R^{14}$ are independently selected from $CH_2$—$CH_2$, $CH_2$—$CHR^a$, $CHR^a$—$CH_2$, $CHR^a$—$CHR^b$, $CHR^a$—$CR^bR^c$, $CR^aR^b$—$CHR^c$, $CR^aR^b$—$CR^cR^d$ or $(CH_2)_e$, where e=2-6, and $R^a$, $R^b$, $R^c$, $R^d$ are lower alkyl groups and $R^a$, $R^b$, $R^c$ and $R^d$ may be the same or different;

$R^{12}$ is H, a lower alkyl, phenyl, substituted phenyl or 1,1-dimethyl-3-oxobutyl group;

X is O or $NR^f$, where $R^f$ is H or a lower alkyl group;

s is 0 or $s \geq 2$; and $o+p+q=100$, $0<o, p, q<100$.

2. The separation system of claim 1, wherein, in the polymer of formula I, unit D is derived from methoxyethyl (meth)acrylate.

3. The separation system of claim 1, wherein, in the polymer of formula I, unit E is derived from one or more of N, N-diethylaminoethyl (meth)acrylate, N, N-dimethylaminoethyl (meth)acrylate, or N, N-dimethylaminopropyl (meth)acrylamide.

4. The separation system of claim 1, wherein, in the polymer of formula I, unit F is derived from one or more of methyl (meth)acrylate, di(ethylene glycol) ethyl ether (meth)acrylate, N-(1,1-dimethyl-3-oxobutyl)-(meth)acrylamide, dimethyl(meth)acrylamide, 2-hydroxyethyl (meth)acrylate, or styrene.

5. The separation system of claim 1, wherein the polymer of formula I comprises:
20-80% by mol of D;
10-40% by mol of E; and
10-40% by mol of F.

6. The separation system of claim 1, wherein the separation medium comprises a membrane or fiber consisting of or coated with the polymer of general formula (II).

7. The separation system of claim 1, wherein the separation medium comprises a non-woven web of fibers consisting of or coated with said polymer of general formula (II).

8. The separation system of claim 6, wherein the container is in the form of a filter casing.

9. Method for the selective removal, reduction or separation of white blood cells and/or platelets from blood which comprises passing blood through the system of claim 6.

10. A ternary polymer of general formula (II):

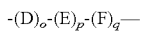 (II)

in which

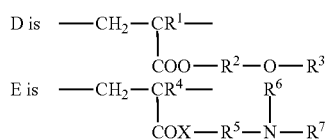

F is selected from

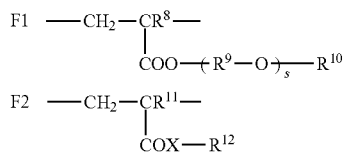

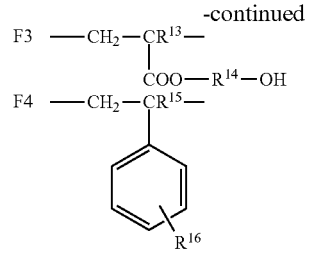

in which $R^1$ is H or a lower alkyl group;

$R^3$, $R^{10}$ are independently lower alkyl, phenyl or substituted phenyl groups;

$R^4$, $R^6$, $R^7$, $R^8$, $R^{11}$, $R^{13}$, $R^{15}$, $R^{16}$ are independently H, lower alkyl, phenyl or substituted phenyl groups;

$R^2$, $R^5$, $R^9$, $R^{14}$ are independently selected from $CH_2$—$CH_2$, $CH_2$—$CHR^a$, $CHR^a$—$CH_2$, $CHR^a$—$CHR^b$, $CHR^a$—$CR^bR^c$, $CR^aR^b$—$CHR^c$, $CR^aR^b$—$CR^cR^d$ or $(CH_2)_e$, where $e=2$-$6$, and $R^a$, $R^b$, $R^c$, $R^d$ are lower alkyl groups and $R^a$, $R^b$, $R^c$ and $R^d$ may be the same or different;

$R^{12}$ is H, a lower alkyl, phenyl, substituted phenyl or 1,1-dimethyl-3-oxobutyl group;

X is O or $NR^f$, where $R^f$ is H or a lower alkyl group;

s is 0 or $s \geq 2$; and $o+p+q=100$, $0<o, p, q<100$.

11. The polymer of claim 10, wherein unit D is derived from methoxyethyl (meth)acrylate.

12. The polymer of claim 10, wherein unit E is derived from one or more of N, N-diethylaminoethyl (meth)acrylate, N, N-dimethylaminoethyl (meth)acrylate, or N, N-dimethylaminopropyl (meth)acrylamide.

13. The polymer of claim 10, wherein unit F is derived from one or more of methyl (meth)acrylate, di(ethylene glycol) ethyl ether (meth)acrylate, N-(1,1-dimethyl-3-oxobutyl)-(meth)acrylamide, dimethyl(meth)acrylamide, 2-hydroxyethyl (meth)acrylate, or styrene.

14. The polymer of claim 10, comprising
20-80% by mol of D;
10-40% by mol of E; and
10-40% by mol of F.

15. The separation system of claim 1, wherein the surface portion consists of the polymer of general formula II.

16. The separation system of claim 6, wherein the membrane or fiber consists of a general purpose polymer completely covered by the polymer of general formula II.

17. The separation system of claim 7, wherein the fibers consist of a general purpose polymer completely covered by the polymer of general formula II.

* * * * *